US012694957B1

(12) United States Patent     (10) Patent No.:   US 12,694,957 B1

Nguyen     (45) Date of Patent:     Jul. 28, 2026

(54) SYSTEM AND METHOD FOR ITERATIVE CLASSIFICATION PARAMETER GENERATION BASED ON REAL-TIME PHYSIOLOGICAL AND AUDIO INTERVIEW DATA

(71) Applicant: Predicate AI Labs Inc., Durham, NC (US)

(72) Inventor: Morris Nguyen, Wilmington, NC (US)

(73) Assignee: PREDICATE AI LABS LTD., Dublin (IE)

( * ) Notice: Subject to any disclaimer, the term of this patent is extended or adjusted under 35 U.S.C. 154(b) by 0 days.

(21) Appl. No.: 19/186,222

(22) Filed: Apr. 22, 2025

Related U.S. Application Data

(63) Continuation of application No. 18/388,237, filed on Nov. 9, 2023, now abandoned.

(51) Int. Cl.
    *G16H 10/60*     (2018.01)
    *A61B 5/00*     (2006.01)
          (Continued)

(52) U.S. Cl.
    CPC ........... *G16H 10/60* (2018.01); *A61B 5/7264* (2013.01); *G06F 40/205* (2020.01); *G16H 50/70* (2018.01)

(58) Field of Classification Search
    CPC ............................... G16H 50/70; G16H 10/60
    See application file for complete search history.

(56) References Cited

U.S. PATENT DOCUMENTS

2017/0098051 A1*   4/2017   Balram ................. G16H 50/20
2017/0293740 A1*   10/2017   Xing .................... G06Q 20/204

(Continued)

OTHER PUBLICATIONS

Final Rejection issued Aug. 1, 2025 in corresponding U.S. Appl. No. 18/769,768. [Available in IFW].

*Primary Examiner* — Jay M. Patel

(74) *Attorney, Agent, or Firm* — Venable LLP; Ryan T. Ward

(57) ABSTRACT

A system for generation of diagnosis parameters based on patient-related data, including a processor of a classification server node configured to host a machine learning module and connected to an interview entity node and to at least one medical entity node over a network; and a memory on which are stored machine-readable instructions that when executed by the processor, cause the processor to: acquire sensory data from a plurality of biosensors encapsulated into a patient wearable device; receive patient interview data from the interview entity node comprising audio data generated during patient interview; derive a language metadata from the interview data; parse the interview data based on the language metadata to derive a plurality of key features; query a local patients' database to retrieve local historical patients'-related data related to previous patients' engagements associated with previous interview data based on the plurality of features; generate at least one feature vector based on the plurality of features, the sensory data and the local historical patients'-related data; and provide the at least one feature vector to the ML module configured to generate a predictive model for producing at least one diagnosis parameter for generation of the patient-related classification for the at least one medical entity node.

20 Claims, 7 Drawing Sheets

(51) Int. Cl.
    *G06F 40/205*       (2020.01)
    *G16H 50/70*       (2018.01)

(56)             References Cited

U.S. PATENT DOCUMENTS

| 2019/0295723 | A1 | | 9/2019 | Bill | |
| 2021/0118559 | A1 | * | 4/2021 | Lefkofsky | G16B 20/00 |
| 2021/0137391 | A1 | | 5/2021 | Mak | |
| 2021/0232361 | A1 | * | 7/2021 | Brown | G06F 3/167 |
| 2021/0327582 | A1 | * | 10/2021 | Joshi | G06Q 10/1093 |
| 2022/0369961 | A1 | * | 11/2022 | Mothilal | A61B 5/7282 |
| 2023/0230685 | A1 | | 7/2023 | Little et al. | |
| 2023/0238019 | A1 | | 7/2023 | Lisic et al. | |
| 2024/0029883 | A1 | * | 1/2024 | Alibakhsh | H04L 41/22 |
| 2024/0062902 | A1 | | 2/2024 | Agrawal et al. | |

* cited by examiner

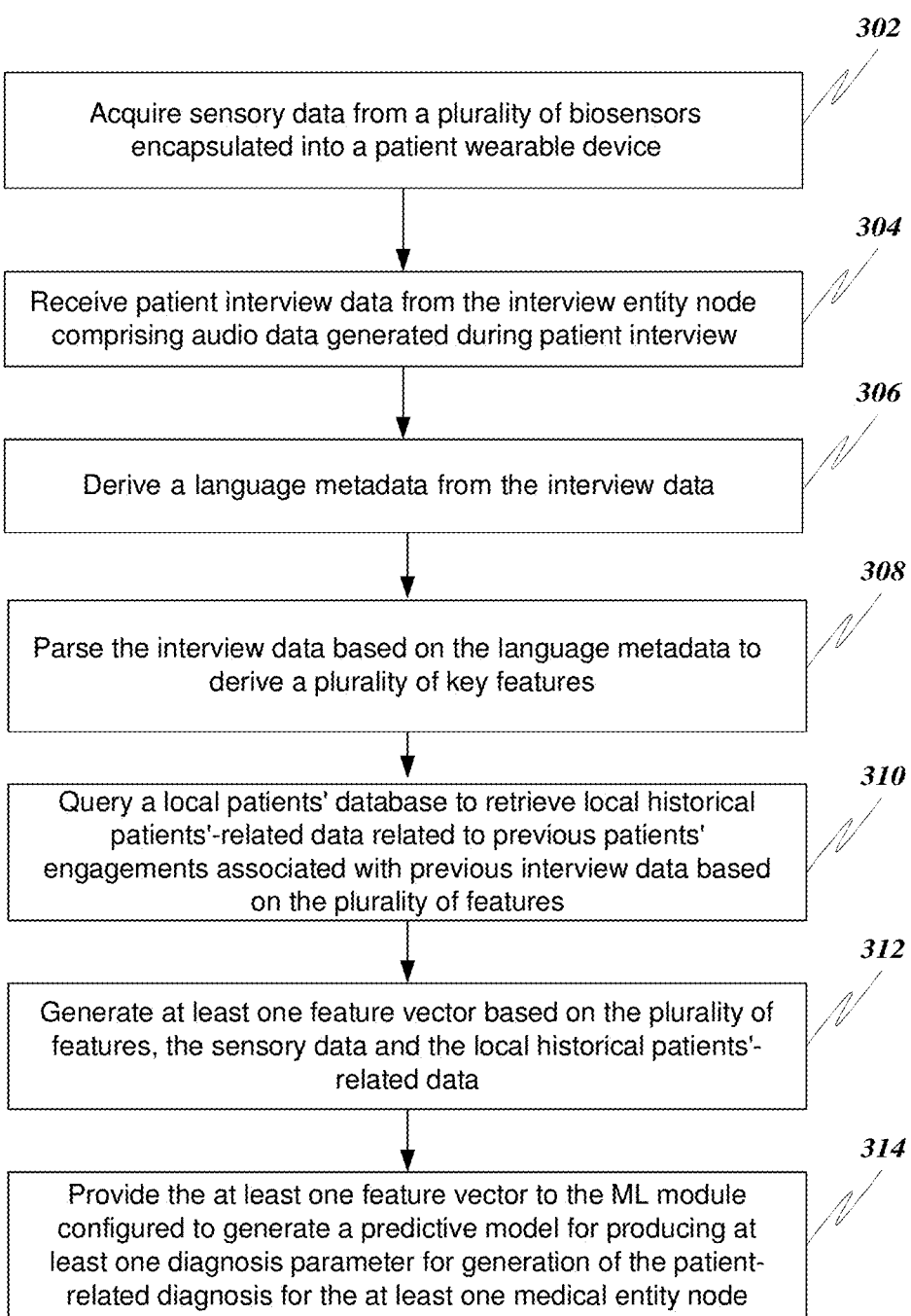

300

302

Acquire sensory data from a plurality of biosensors encapsulated into a patient wearable device

304

Receive patient interview data from the interview entity node comprising audio data generated during patient interview

306

Derive a language metadata from the interview data

308

Parse the interview data based on the language metadata to derive a plurality of key features

310

Query a local patients' database to retrieve local historical patients'-related data related to previous patients' engagements associated with previous interview data based on the plurality of features

312

Generate at least one feature vector based on the plurality of features, the sensory data and the local historical patients'-related data

314

Provide the at least one feature vector to the ML module configured to generate a predictive model for producing at least one diagnosis parameter for generation of the patient-related diagnosis for the at least one medical entity node

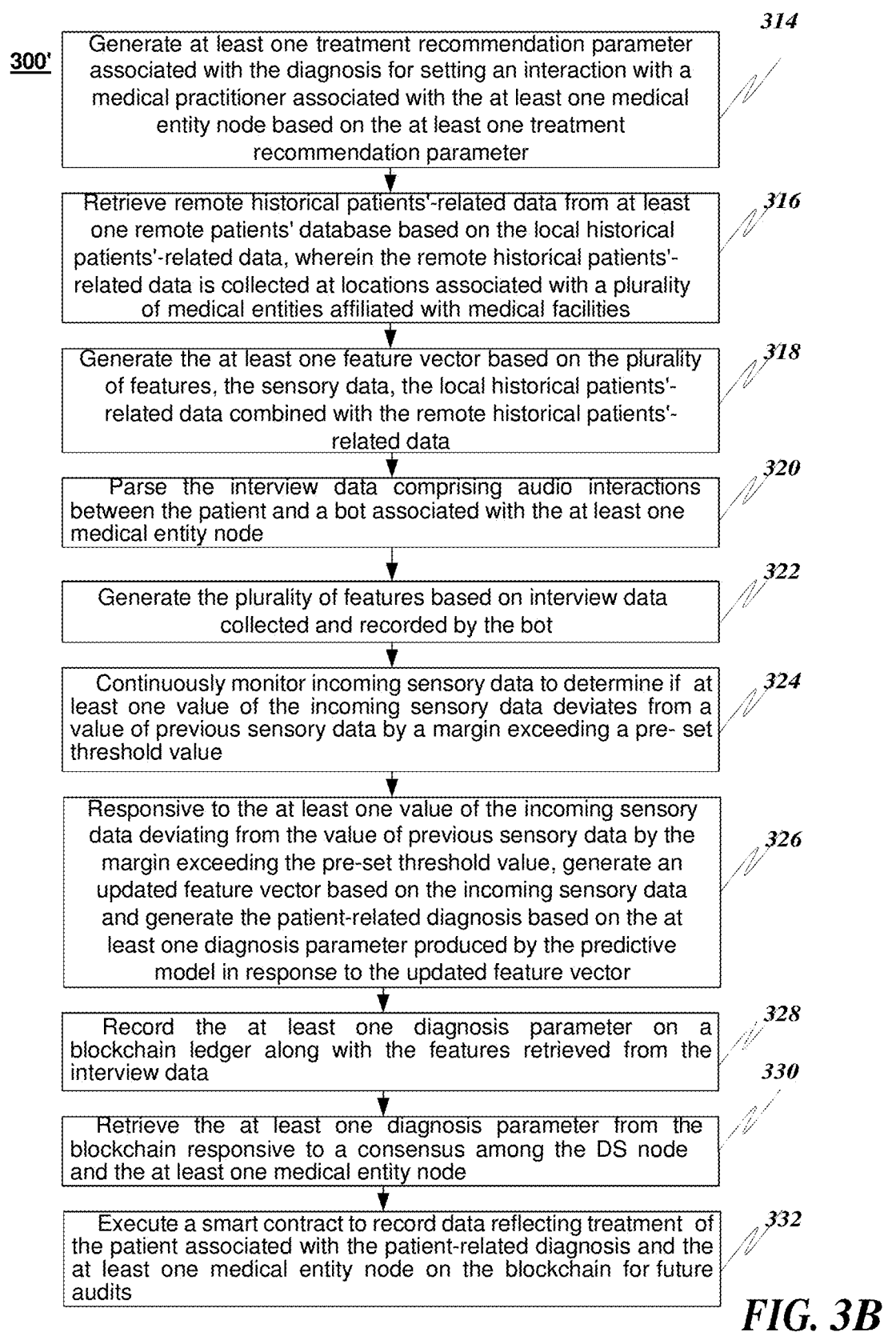

Generate at least one treatment recommendation parameter associated with the diagnosis for setting an interaction with a medical practitioner associated with the at least one medical entity node based on the at least one treatment recommendation parameter

316

Retrieve remote historical patients'-related data from at least one remote patients' database based on the local historical patients'-related data, wherein the remote historical patients'-related data is collected at locations associated with a plurality of medical entities affiliated with medical facilities

318

Generate the at least one feature vector based on the plurality of features, the sensory data, the local historical patients'-related data combined with the remote historical patients'-related data

320

Parse the interview data comprising audio interactions between the patient and a bot associated with the at least one medical entity node

322

Generate the plurality of features based on interview data collected and recorded by the bot

324

Continuously monitor incoming sensory data to determine if at least one value of the incoming sensory data deviates from a value of previous sensory data by a margin exceeding a pre- set threshold value

326

Responsive to the at least one value of the incoming sensory data deviating from the value of previous sensory data by the margin exceeding the pre-set threshold value, generate an updated feature vector based on the incoming sensory data and generate the patient-related diagnosis based on the at least one diagnosis parameter produced by the predictive model in response to the updated feature vector

328

Record the at least one diagnosis parameter on a blockchain ledger along with the features retrieved from the interview data

330

Retrieve the at least one diagnosis parameter from the blockchain responsive to a consensus among the DS node and the at least one medical entity node

332

Execute a smart contract to record data reflecting treatment of the patient associated with the patient-related diagnosis and the at least one medical entity node on the blockchain for future audits

*FIG. 3B*

400
402
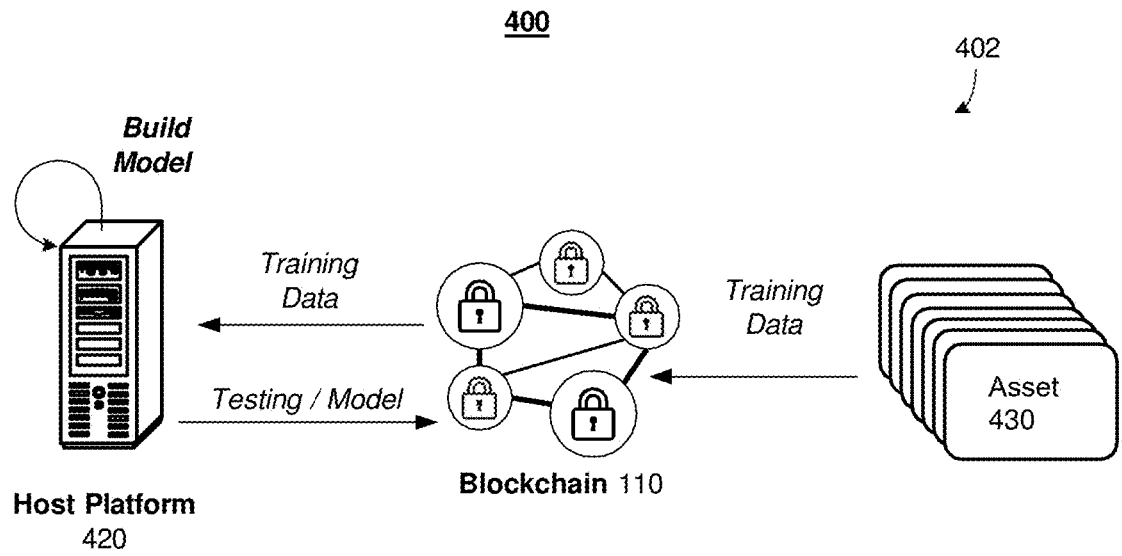
404
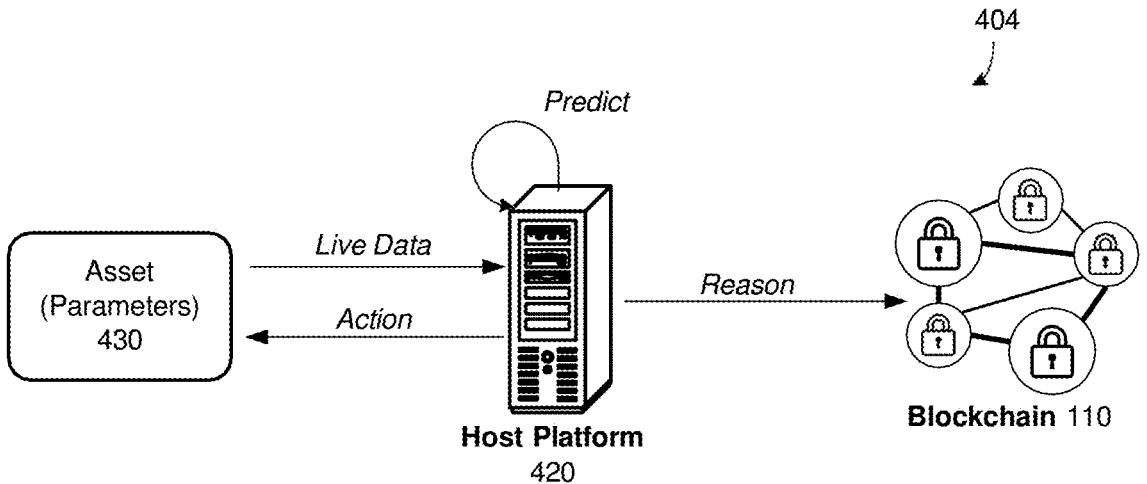
*FIG. 4*

1

SYSTEM AND METHOD FOR ITERATIVE CLASSIFICATION PARAMETER GENERATION BASED ON REAL-TIME PHYSIOLOGICAL AND AUDIO INTERVIEW DATA

FIELD OF DISCLOSURE

The present disclosure generally relates to systems and methods for generation of classification parameters based on collected patient-related data, and more particularly, to a computing system configured to perform real-time classification parameter generation using predictive modeling techniques applied to physiological sensor data and patient interview data.

BACKGROUND

The process of computerized disease detection and classification (e.g., diagnosis), for example of a septic condition, through implementation of a data collection system is commonly used. This process requires processing and recording of patient-related medical data.

For example, U.S. Pat. No. 9,968,289 to SANMINA CORPORATION discloses a biosensor including an optical sensor circuit that emits light directed at skin tissue of a patient at a plurality of wavelengths. A first and second spectral response of light reflected from the tissue is obtained around a first wavelength in a UV range and a second wavelength in an IR range. A measurement of nitric oxide (NO) is then determined from the spectral responses. A risk of septic condition is obtained using the measurement of NO.

U.S. Pat. No. 11,504,071 B2 to Hill-Rom Services discloses an apparatus for assessing medical risks of a patient includes an analytics engine and equipment that provides data to the analytics engine. The equipment includes a patient support apparatus such as a patient bed, a nurse call computer, a physiological monitor, a patient lift, a locating computer of a locating system, and an incontinence detection pad. The analytics engine analyzes the data from the equipment to determine a sepsis risk score, a falls risk score, and a pressure injury score. The apparatus further includes displays that are communicatively coupled to the analytics engine and that display the sepsis, falls, and pressure injury risk scores. The displays include a status board display located at a master nurse station, an in-room display provided by a room station of a nurse call system, an electronic medical records (EMR) display of an EMR computer, and a mobile device display of a mobile device of a caregiver assigned to the patient.

US Patent Application No. US 2021/0106287 A1 to University of Virginia Patent Foundation discloses a method and system for generating pulse oximetry predictive scores for predicting adverse outcomes in preterm infants including sepsis.

While these patents address various aspects of sepsis detection based on data extraction, processing, and automation, they may not fully account for the challenges associated with automated detection and classification. The existing solutions while using some sort of automated analytics, do not process the audio interview data of the patient in combination with sensory data acquired from a wearable device. Additionally, these patents do not mention the use of fine-tuned models based on pre-trained language models used to handle the extraction and processing of patient interview information, which can offer a significant improvement in accuracy and efficiency compared to traditional data-based classification techniques.

Accordingly, a system and method for automated real-time classification based on predictive analytics of patient interview data and sensory patient-related data are desired.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

One embodiment of the present disclosure provides a system for generation of classification based on patient-related data, including a processor of a classification server (CS) node configured to host a machine learning (ML) module and connected to an interview entity node and to at least one medical entity node over a network; and a memory on which are stored machine-readable instructions that when executed by the processor, cause the processor to: acquire sensory data from a plurality of biosensors encapsulated into a patient wearable device; receive patient interview data from the interview entity node comprising audio data generated during patient interview; derive a language metadata from the interview data; parse the interview data based on the language metadata to derive a plurality of key features; query a local patients' database to retrieve local historical patients'-related data related to previous patients' engagements associated with previous interview data based on the plurality of features; generate at least one feature vector based on the plurality of features, the sensory data and the local historical patients'-related data; and provide the at least one feature vector to the ML module configured to generate a predictive model for producing at least one diagnosis parameter for generation of the patient-related classification for the at least one medical entity node.

Another embodiment of the present disclosure provides a method that includes one or more of: acquiring sensory data from a plurality of biosensors encapsulated into a patient wearable device; receiving patient interview data from the interview entity node comprising audio data generated during patient interview; deriving a language metadata from the interview data; parsing the interview data based on the language metadata to derive a plurality of key features; querying a local patients' database to retrieve local historical patients'-related data related to previous patients' engagements associated with previous interview data based on the plurality of features; generating at least one feature vector based on the plurality of features, the sensory data and the local historical patients'-related data; and providing the at least one feature vector to the ML module configured to generate a predictive model for producing at least one diagnosis parameter for generation of the patient-related classification for the at least one medical entity node.

Another embodiment of the present disclosure provides a computer-readable medium including instructions for acquiring sensory data from a plurality of biosensors encapsulated into a patient wearable device; receiving patient interview data from the interview entity node comprising audio data generated during patient interview; deriving a language metadata from the interview data; parsing the interview data based on the language metadata to derive a plurality of key features; querying a local patients' database to retrieve local historical patients'-related data related to previous patients' engagements associated with previous interview data based on the plurality of features; generating at least one feature vector based on the plurality of features, the sensory data and the local historical patients'-related data; and providing the at least one feature vector to the ML module configured to generate a predictive model for producing at least one diagnosis parameter for generation of the patient-related classification for the at least one medical entity node.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings:

FIG. 3A illustrates a flowchart of a method for a patient classification based on interview-related data and patient-related sensory data consistent with the present disclosure;

FIG. 3B illustrates a further flowchart of a method for a patient classification based on interview-related data and patient-related sensory data consistent with the present disclosure;

FIG. 4 illustrates deployment of a machine learning model for prediction of diagnosis-related parameters using blockchain assets consistent with the present disclosure;

DETAILED DESCRIPTION

Figure 1A:
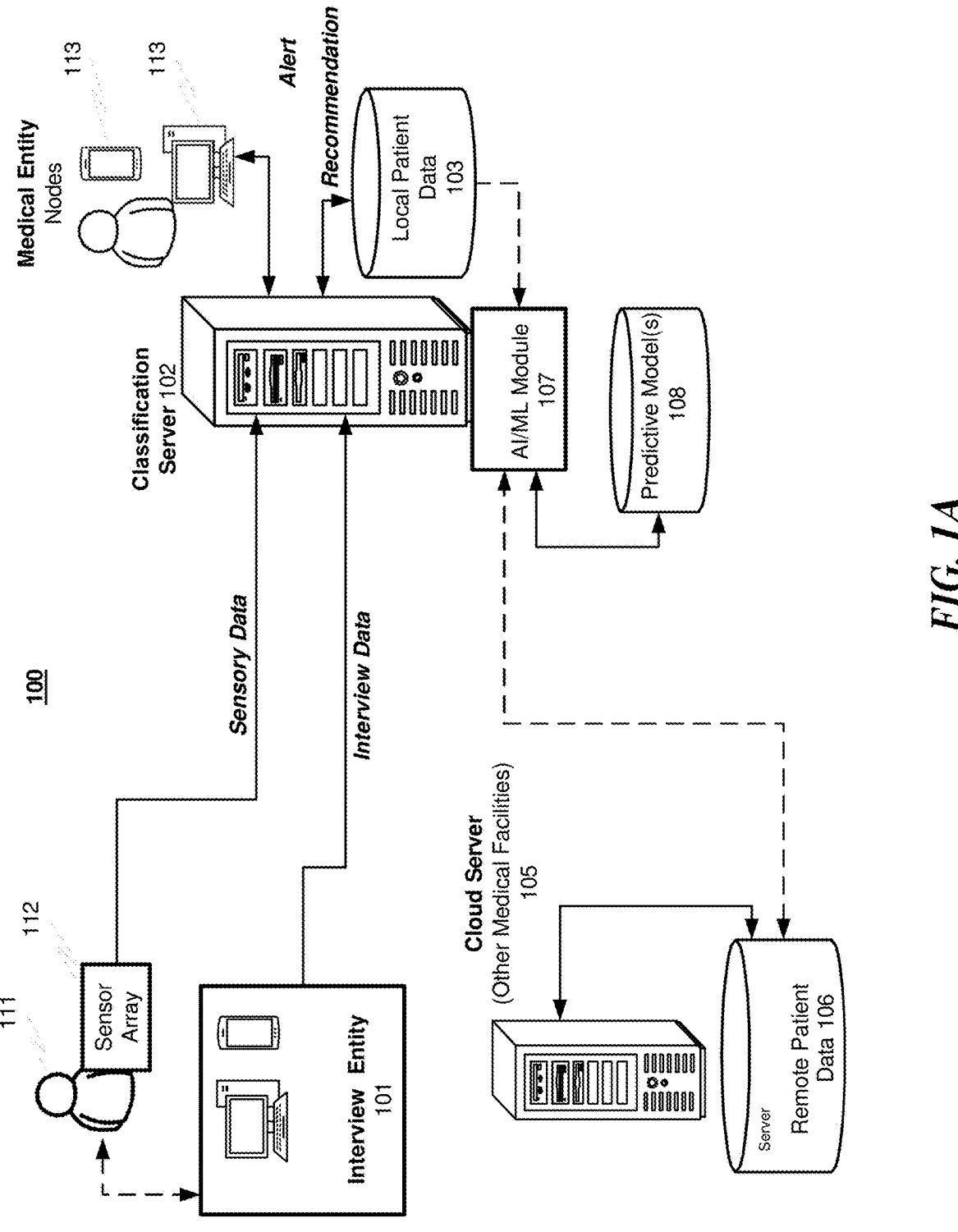
FIG. 1A illustrates a network diagram of a system for a patient classification based on interview-related data and patient-related sensory data consistent with the present disclosure.

This application is related to U.S. patent application Ser. No. 18/388,237, filed Nov. 9, 2023, the entirety of which is incorporated herein by reference.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such a term to mean based on the contextual use of such term herein. To the extent that the meaning of a term used herein—as understood by the ordinary artisan based on the contextual use of such term-differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

The present disclosure includes many aspects and features. Moreover, while many aspects and features relate to, and are described in the context of the sepsis classification, embodiments of the present disclosure are not limited to use only in this context.

The present disclosure provides a system, method and computer-readable medium for AI-based automated classification (e.g., diagnosis) based on patient-related data. In one embodiment, the system overcomes the limitations of existing patient data processing methods by employing fine-tuned models derived from pre-trained language models to extract and process the patient interview information, irrespective of data format, style, or data type. By leveraging the capabilities of the pre-trained language models and classification models, the disclosed approach offers a significant improvement over existing solutions discussed above in the background section.

In one embodiment of the present disclosure, the system provides for AI and machine learning (ML)-generated parameters based on analysis of a patient-related data. In one embodiment, an automated decision/classification model may be generated to provide for treatment recommendation parameters associated with the patient. The automated decision/classification model may use historical patients' data collected at the current medical facility location (i.e., a clinic or hospital entity) and at medical facilities of the same type located within a certain range from the current location or even located globally. The relevant patients' data may include data related to other patients having the same parameters such as age, race, gender, medical conditions, language or locations, etc. The relevant patients' data may indicate successfully treated cases and indication of a practitioner (i.e., a general physician, a specialist, or a nurse practitioner) who treated the patient and the facility where the treatment was performed. This way, the best matching medical practitioner may be directed to respond to a given patient based on current patient-related data and historical data of treating patients having the same characteristics such as gender, race, age, language, condition, location, etc.

In one disclosed embodiment, the A I/M L technology may be combined with a blockchain technology for secure use of the patient-related data and patient-related interview data. In one embodiment, the medical practitioner entities may be connected to the classification server (CS) node over a blockchain network to achieve a consensus prior to executing a transaction to release the classification and treatment recommendation for the patient based on the diagnosis parameters produced by the AI/ML module. The system may utilize patient and/or patient-related data assets based on the patient entity and the medical practitioners' entities being on-boarded to the system via a blockchain network.

The disclosed process according to one embodiment may, advantageously, eliminate the need for the medical practitioners to analyze the patient-related data using transcripts produced by the NPL processing. Instead, the classification and treatment recommendations may be produced directly on a granular level based on patient and patient interview-associated digital data according to the A I-based predictive analysis and treatment recommendations.

This process includes a transparent recommendations/ classification mechanism that may be coupled with a secure communications chat channel (implemented over a blockchain network) which supports both parties to set and agree on the treatment procedures and terms of administering medical services or products with each other. In one embodiment, the chat channel may be implemented using a chat Bot.

As discussed above, the disclosed embodiments provide a process for detecting conditions such as sepsis by analyzing aggregated data from app-based automatic speech recognition and wearable sensors using AI techniques. The disclosed method involves the following steps:

1. Wearable biosensor/physiological monitoring;
2. Digital scribe using app-based, voice artificial technology (ambient note generation) to listen to clinician-patient interactions/interview in real-time;
3. Preprocessing of aggregated sensor data and transcribed clinical notes to remove noise and artifacts using signal filtering and data normalization techniques;
4. Feature extraction using keyword matching from the clinical notes, and capturing physiological patterns and changes from biosensor data that indicate sepsis;
5. AI-based analysis that continuously learns and adapts to optimize the accuracy and reliability of the detection process;
6. Sepsis risk assessment modeling; and
7. Alert generation and notification.

FIG. 1A illustrates a network diagram of a system for a patient classification based on interview-related data and patient-related sensory data consistent with the present disclosure. In some cases, it is a system for a AI-based patient classification.

Referring to FIG. 1A, the example network 100 includes the classification server (CS) node 102 connected to a cloud server node(s) 105 over a network. The CS node 102 is configured to host an AI/ML module 107. The CS node 102 may receive sensory data from an array of biosensors 112 implemented on a wearable device used by a patient 111. The CS node 102 may receive interview data related to communication between the patient 111 and an interview entity 101.

The interview data may have language indicator metadata representing the language of the patient used during the interview. In one embodiment, the interview data may be processed by the CS node 102 using the pre-trained large language models. The CS node 102 may derive the language indicator and parse out the interview data based on the language indicator metadata. In other words, the key features of the interview data may be derived from the interview data based on the language of the interview.

In one embodiment, the language indicator may serve as a kind of a linguistic profile associated with the interview. The language indicator may guide the AI/ML module 107 in dynamically tailoring the processing methods. Depending on the language indicated, the CS node 102 could engage specialized language models or apply unique natural language processing techniques optimized for that language.

Regarding the global reach of the disclosed system and method, a cultural intelligence layer may be added to the language indicator. The goal is for the system to not only recognize the language, but also adapt its recommendations and interactions to be culturally sensitive and appropriate. In one embodiment the disclosed system may employ integrated translation capabilities. This may allow both the patient 111 and the interview entity 101 to communicate effortlessly, no matter where they are in the world or what languages they use. The language indicator may initiate this feature, making the system truly globally effective.

The CS node 102 may query a local patient database for the historical local patients' data 103 associated with the current patient 111 data. The CS node 102 may acquire relevant remote patients' data 106 from a remote database residing on a cloud server 105. The remote patients' data 106 may be collected from other medical facilities. The remote patients' data 106 may be collected from the patients of the same (or similar) condition, age, gender, race, language, etc. as the local patients' who are associated with the current patient-related data of the patient 111.

The CS node 102 may generate a feature vector or classifier data based on the patient-related sensory data, patient 111 interview data and the collected patients' data (i.e., pre-stored local data 103 and remote data 106). The CS node 102 may ingest the feature vector data into an AI/ML module 107. The AI/ML module 107 may generate a predictive model(s) 108 based on the feature vector data to predict diagnosis parameters for automatically generating a classification and treatment recommendation to be provided to the medical entities 113 (e.g., physicians, specialist, nurse practitioners, etc.). The diagnosis and/or risk assessment parameters may be further analyzed by the CS node 102 prior to generation of the classification. In one embodiment, the diagnosis parameters may be used for adjustment of the treatment response based on availability of the patient and a medical practitioner. Once the classification is determined, an alert/notification may be sent to the medical entity 113. The appointment with the practitioner associated with the medical entity 113 may be scheduled based on treatment urgency and risk assessment.

Figure 1B:
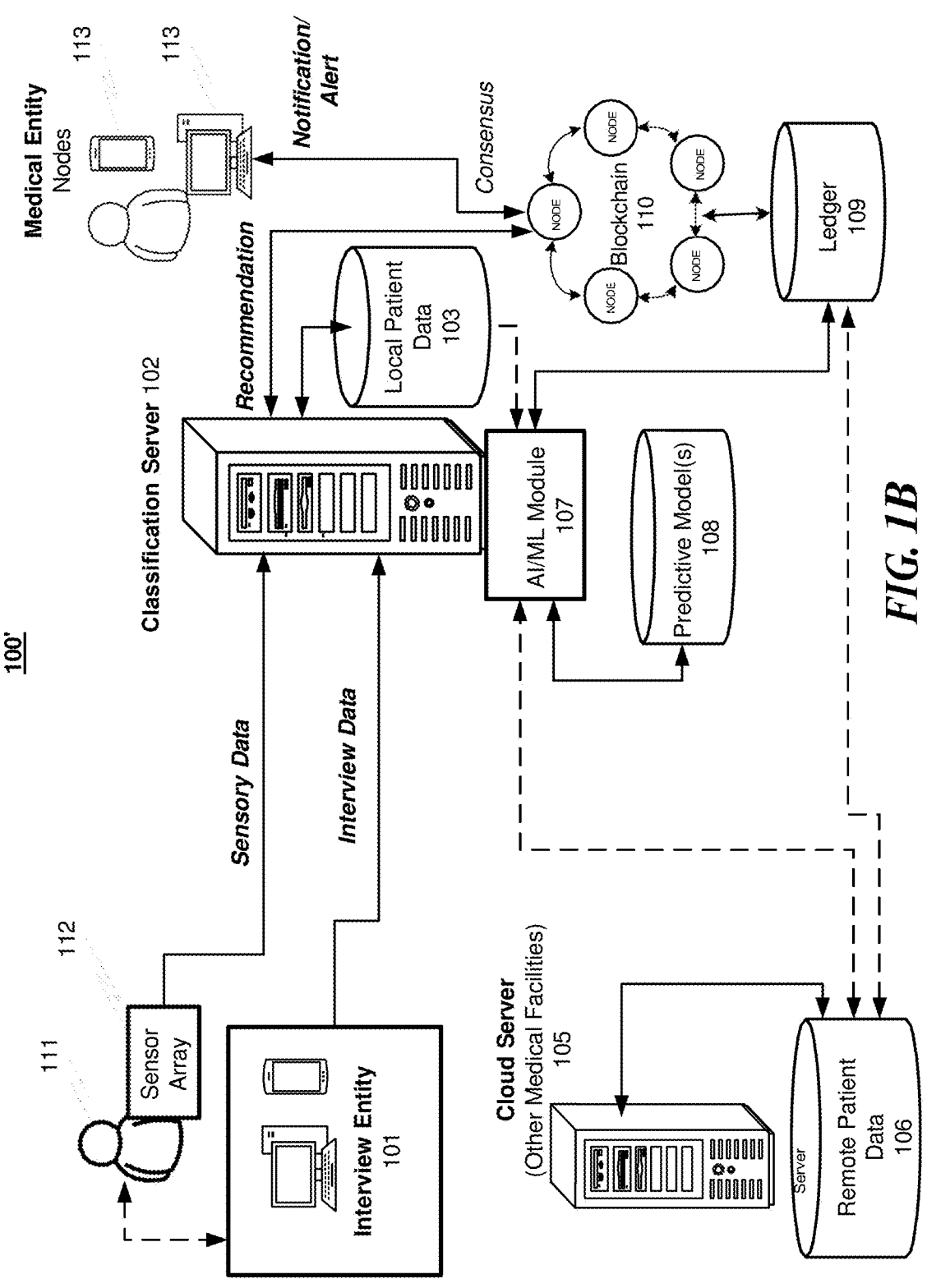
FIG. 1B illustrates a network diagram of a system for a patient classification based on interview-related data and patient-related sensory data implemented over a blockchain consistent with the present disclosure.

FIG. 1B illustrates a network diagram of a system for a patient classification based on interview-related data and patient-related sensory data implemented over a blockchain consistent with the present disclosure.

Referring to FIG. 1B, the example network 100' includes the classification server (CS) node 102 connected to a cloud server node(s) 105 over a network. The CS node 102 is configured to host an AI/ML module 107. The CS node 102 may receive sensory data from an array of biosensors 112 implemented on a wearable device used by a patient 111. The CS node 102 may receive interview data related to communication between the patient 111 and an interview entity 101.

The interview data may have language indicator metadata representing the language of the patient used during the interview. In one embodiment, the interview data may be processed by the CS node 102 using the pre-trained large language models. The CS node 102 may derive the language indicator and parse out the interview data based on the language indicator metadata. In other words, the key features of the interview data may be derived from the interview data based on the language of the interview.

In one embodiment, the language indicator may serve as a kind of a linguistic profile associated with the interview. The language indicator may guide the AI/ML module 107 in dynamically tailoring the processing methods. Depending on the language indicated, the CS node 102 could engage specialized language models or apply unique natural language processing techniques optimized for that language.

Regarding the global reach of the disclosed system and method, a cultural intelligence layer may be added to the language indicator. The goal is for the system to not only recognize the language, but also adapt its recommendations and interactions to be culturally sensitive and appropriate. In one embodiment the disclosed system may employ integrated translation capabilities. This may allow both the patient 111 and the interview entity 101 to communicate effortlessly, no matter where they are in the world or what languages they use. The language indicator may initiate this feature, making the system truly globally effective.

The CS node 102 may query a local patient database for the historical local patients' data 103 associated with the current patient 111 data. The CS node 102 may acquire relevant remote patients' data 106 from a remote database residing on a cloud server 105. The remote patients' data 106 may be collected from other medical facilities. The remote patients' data 106 may be collected from the patients of the same (or similar) condition, age, gender, race, language, etc. as the local patients' who are associated with the current patient-related data of the patient 111.

The CS node 102 may generate a feature vector or classifier data based on the patient-related sensory data, patient 111 interview data and the collected patients' data (i.e., pre-stored local data 103 and remote data 106). The CS node 102 may ingest the feature vector data into an AI/ML module 107. The AI/ML module 107 may generate a predictive model(s) 108 based on the feature vector data to predict diagnosis parameters for automatically generating a classification and treatment recommendation to be provided to the medical entities 113 (e.g., physicians, specialist, nurse practitioners, etc.). The diagnosis and/or risk assessment parameters may be further analyzed by the CS node 102 prior to generation of the classification.

In one embodiment, the CS node 102 may receive the predicted diagnosis parameters from a permissioned blockchain 110 ledger 109 based on a consensus from the medical entity nodes 113 confirming, for example, classification, treatment plan, schedule and patient condition. Additionally, confidential historical patient-related information and previous patients'-related diagnosis parameters may also be acquired from the permissioned blockchain 110. The newly acquired patient-related data with corresponding predicted classification and treatment recommendation parameters data may be also recorded on the ledger 109 of the blockchain 110 so it can be used as training data for the predictive model(s) 108. In this implementation the CS node 102, the cloud server 105, the medical entity nodes 113 and interview entities(s) 101 may serve as blockchain 110 peer nodes. In one embodiment, local patients' data 103 and remote patients' data 106 may be duplicated on the blockchain ledger 109 for higher security of storage.

The AI/ML module 107 may generate a predictive model(s) 108 to predict the classification and treatment recommendation parameters for the patient 111 in response to the specific relevant pre-stored patients'-related data acquired from the blockchain 110 ledger 109. This way, the current classification and treatment parameters may be predicted based not only on the current patient-related sensory data and current interview data, but also based on the previously collected heuristics and patients'-related data associated with the given patient 111 data or current diagnosis parameters generated based on the patient sensory data and interview data. This way, the most optimal way of handling the patient, such as the best medical specialist(s) is selected for treating the patient 111, for the most likely successful treatment.

Figure 2:
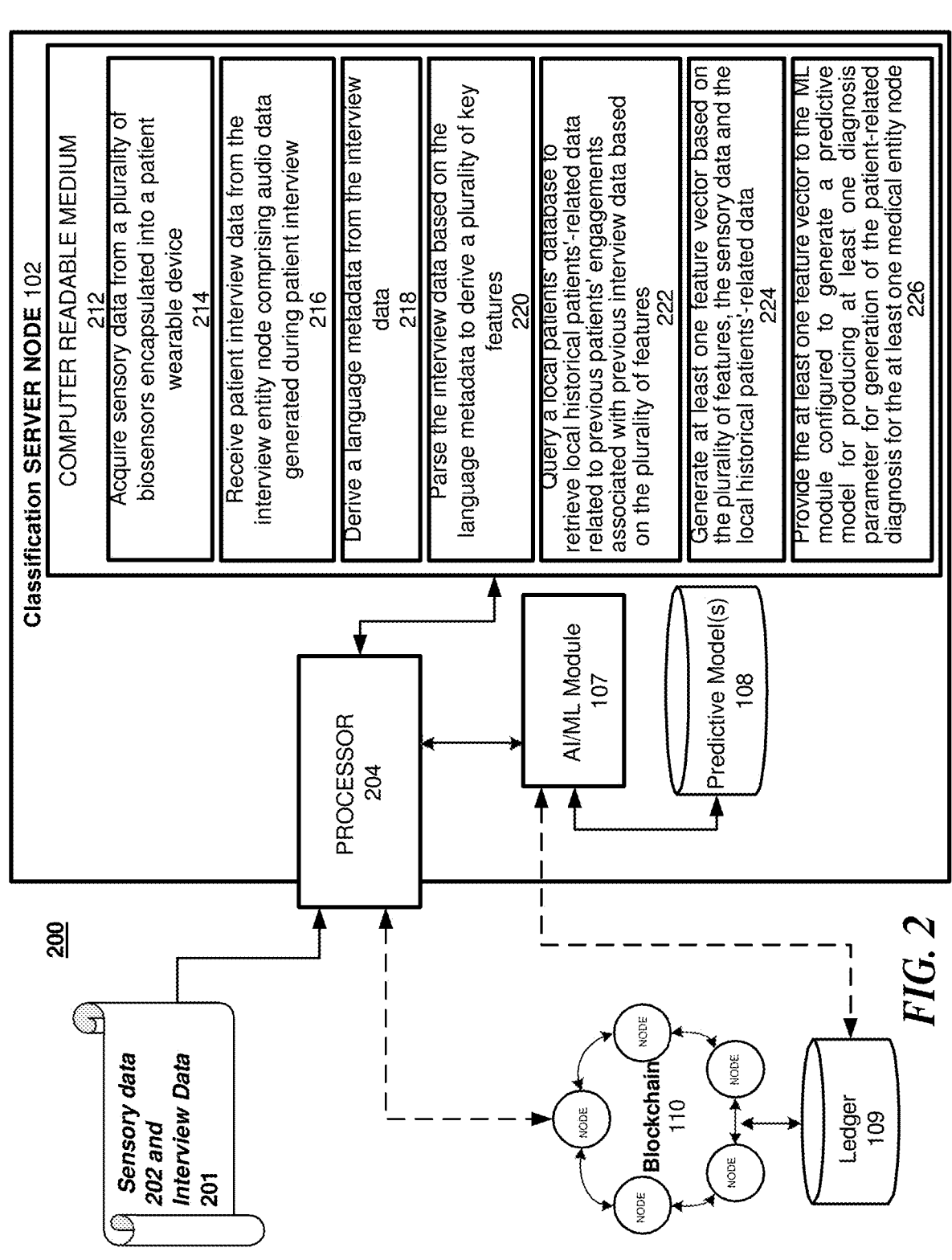
FIG. 2 illustrates a network diagram of a system including detailed features of a classification server (CS) node consistent with the present disclosure.

FIG. 2 illustrates a network diagram of a system including detailed features of a classification server (CS) node consistent with the present disclosure.

Referring to FIG. 2, the example network 200 includes the CS node 102 connected to an interview entity 101 to receive interview data 201. The CS node 102 is also connected to an array of bio-sensors implemented on a patient wearable device (not shown) to receive sensory data 202.

The CS node 102 is configured to host an AI/ML module 107. As discussed above with respect to FIGS. 1A-B, the CS node 102 may receive the interview data provided by the interview entities 101 (FIG. 1A) and pre-stored patients' data retrieved from local and remote databases. As discussed above, the pre-stored patients' data may be retrieved from the ledger 109 of the blockchain 110.

The AI/ML module 107 may generate a predictive model(s) 108 based on the received patient-related data 201 and 202 and the patients'-related data provided by the CS node 102. As discussed above, the AI/ML module 107 may provide predictive outputs data in the form of diagnosis parameters for automatic generation of patient treatment recommendations for the medical entities 113 (see FIG. 1B). The CS node 102 may process the predictive outputs data received from the AI/ML module 107 to generate the classification and treatment or risk assessment recommendation pertaining to a particular patient engagement.

In one embodiment, the CS node 102 may acquire sensory data from the bio sensor array periodically in order to check if new classification or treatment recommendations need to be generated or the treatment schedule needs to be reset. In another embodiment, the CS node 102 may continually monitor sensory data and may detect a parameter that deviates from a previous recorded parameter (or from a median reading value) by a margin that exceeds a threshold value pre-set for this particular parameter. For example, if a patient's temperature and hear rate changes, this may cause a change in classification or risk assessment. Accordingly, once the threshold is met or exceeded by at least one parameter of the patient, the CS node 102 may provide the currently acquired patient parameter to the AI/ML module 107 to generate an updated classification or treatment recommendation parameters based on the current patient's conditions and updated risk assessment parameters.

While this example describes in detail only one CS node 102, multiple such nodes may be connected to the network and to the blockchain 110. It should be understood that the CS node 102 may include additional components and that some of the components described herein may be removed and/or modified without departing from a scope of the CS node 102 disclosed herein. The CS node 102 may be a computing device or a server computer, or the like, and may include a processor 204, which may be a semiconductor-based microprocessor, a central processing unit (CPU), an application specific integrated circuit (ASIC), a field-programmable gate array (FPGA), and/or another hardware device. Although a single processor 204 is depicted, it should be understood that the CS node 102 may include multiple processors, multiple cores, or the like, without departing from the scope of the CS node 102 system.

The CS node 102 may also include a non-transitory computer readable medium 212 that may have stored thereon machine-readable instructions executable by the processor 204. Examples of the machine-readable instructions are shown as 214-226 and are further discussed below.

Examples of the non-transitory computer readable medium 212 may include an electronic, magnetic, optical, or other physical storage device that contains or stores executable instructions. For example, the non-transitory computer readable medium 212 may be a Random-Access memory (RAM), an Electrically Erasable Programmable Read-Only Memory (EEPROM), a hard disk, an optical disc, or other type of storage device.

The processor 204 may fetch, decode, and execute the machine-readable instructions 214 to acquire sensory data from a plurality of biosensors encapsulated into a patient wearable device. The processor 204 may fetch, decode, and execute the machine-readable instructions 216 to receive patient interview data from the interview entity node comprising audio data generated during patient interview. The processor 204 may fetch, decode, and execute the machine-readable instructions 218 to derive a language metadata from the interview data. The processor 204 may fetch, decode, and execute the machine-readable instructions 220 to parse the interview data based on the language metadata to derive a plurality of key features.

The processor 204 may fetch, decode, and execute the machine-readable instructions 222 to query a local patients' database to retrieve local historical patients'-related data related to previous patients' engagements associated with previous interview data based on the plurality of features. The processor 204 may fetch, decode, and execute the machine-readable instructions 224 to generate at least one feature vector based on the plurality of features, the sensory data and the local historical patients'-related data. The processor 204 may fetch, decode, and execute the machine-readable instructions 226 to provide the at least one feature vector to the ML module configured to generate a predictive model for producing at least one diagnosis parameter for generation of the patient-related classification for the at least one medical entity node.

The permissioned blockchain 110 may be configured to use one or more smart contracts that manage transactions for multiple participating nodes and for recording the transactions on the ledger 109.

FIG. 3A illustrates a flowchart of a method for a patient classification based on interview-related data and patient-related sensory data consistent with the present disclosure.

Referring to FIG. 3A, the method 300 may include one or more of the steps described below. FIG. 3A illustrates a flow chart of an example method executed by the CS 102 (see FIG. 2). It should be understood that method 300 depicted in FIG. 3A may include additional operations and that some of the operations described therein may be removed and/or modified without departing from the scope of the method 300. The description of the method 300 is also made with reference to the features depicted in FIG. 2 for purposes of illustration. Particularly, the processor 204 of the CS node 102 may execute some or all of the operations included in the method 300.

With reference to FIG. 3A, at block 302, the processor 204 may acquire sensory data from a plurality of biosensors encapsulated into a patient wearable device. At block 304, the processor 204 may receive patient interview data from the interview entity node comprising audio data generated during patient interview. At block 306, the processor 204 may derive a language metadata from the interview data. At block 308, the processor 204 may parse the interview data based on the language metadata to derive a plurality of key features. At block 310, the processor 204 may query a local patients' database to retrieve local historical patients'-related data related to previous patients' engagements associated with previous interview data based on the plurality of features. At block 312, the processor 204 may generate at least one feature vector based on the plurality of features, the sensory data and the local historical patients'-related data. At block 314, the processor 204 may provide the at least one feature vector to the ML module configured to generate a predictive model for producing at least one diagnosis parameter for generation of the patient-related classification for the at least one medical entity node.

FIG. 3B illustrates a further flowchart of a method for a patient diagnosis based on interview-related data and patient-related sensory data consistent with the present disclosure.

Referring to FIG. 3B, the method 300' may include one or more of the steps described below.

FIG. 3B illustrates a flow chart of an example method executed by the CS 102 (see FIG. 2). It should be understood that method 300' depicted in FIG. 3B may include additional operations and that some of the operations described therein may be removed and/or modified without departing from the scope of the method 300'. The description of the method 300' is also made with reference to the features depicted in FIG. 2 for purposes of illustration. Particularly, the processor 204 of the RS 102 may execute some or all of the operations included in the method 300'.

With reference to FIG. 3B, at block 314, the processor 204 may generate at least one treatment recommendation parameter associated with the classification for setting an interaction with a medical practitioner associated with the at least one medical entity node based on the at least one treatment recommendation parameter. At block 316, the processor 204 may retrieve remote historical patients'-related data from at least one remote patients' database based on the local historical patients'-related data, wherein the remote historical patients'-related data is collected at locations associated with a plurality of medical entities affiliated with medical facilities. At block 318, the processor 204 may generate the at least one feature vector based on the plurality of features, the sensory data, the local historical patients'-related data combined with the remote historical patients'-related data. At block 320, the processor 204 may parse the interview data comprising audio interactions between the patient and a bot associated with the at least one medical entity node.

At block 322, the processor 204 may generate the plurality of features based on interview data collected and recorded by the bot. At block 324, the processor 204 may continuously monitor incoming sensory data to determine if at least one value of the incoming sensory data deviates from a value of previous sensory data by a margin exceeding a pre-set threshold value. At block 326, the processor 204 may, responsive to the at least one value of the incoming sensory data deviating from the value of previous sensory data by the margin exceeding the pre-set threshold value, generate an updated feature vector based on the incoming sensory data and generate the patient-related classification based on the at least one diagnosis parameter produced by the predictive model in response to the updated feature vector. At block 328, the processor 204 may record the at least one diagnosis parameter on a blockchain ledger along with the features retrieved from the interview data. At block 330, the processor 204 may retrieve the at least one diagnosis parameter from the blockchain responsive to a consensus among the CS node and the at least one medical entity node. At block 332, the processor 204 may execute a smart contract to record data reflecting treatment of the patient associated with the patient-related classification and the at least one medical entity node on the blockchain for future audits.

In one disclosed embodiment, the diagnosis parameters' model may be generated by the AI/ML module 107 that may use training data sets to improve accuracy of the prediction of the diagnosis parameters for the medical entities 113 (FIG. 1A). The diagnosis parameters used in training data sets may be stored in a centralized local database (such as one used for storing local patients' data 103 depicted in FIG. 1A). In one embodiment, a neural network may be used in the AI/ML module 107 for diagnosis parameters modeling and treatment predictions.

In another embodiment, the AI/ML module 107 may use a decentralized storage such as a blockchain 110 (see FIG. 1B) that is a distributed storage system, which includes multiple nodes that communicate with each other. The decentralized storage includes an append-only immutable data structure resembling a distributed ledger capable of maintaining records between mutually untrusted parties. The untrusted parties are referred to herein as peers or peer nodes. Each peer maintains a copy of the parameter(s) records and no single peer can modify the records without a consensus being reached among the distributed peers. For example, the peers 101, 113 and 102 (FIG. 1B) may execute a consensus protocol to validate blockchain 110 storage transactions, group the storage transactions into blocks, and build a hash chain over the blocks. This process forms the ledger 109 by ordering the storage transactions, as is necessary, for consistency. In various embodiments, a permissioned and/or a permissionless blockchain can be used. In a public or permissionless blockchain, anyone can participate without a specific identity. Public blockchains can involve assets and use consensus based on various protocols such as Proof of Work (PoW). On the other hand, a permissioned blockchain provides secure interactions among a group of entities which share a common goal such as storing diagnosis parameters for efficient treatment of patients, but which do not fully trust one another.

This application utilizes a permissioned (private) blockchain that operates arbitrary, programmable logic, tailored to a decentralized storage scheme and referred to as "smart contracts" or "chaincodes." In some cases, specialized chaincodes may exist for management functions and parameters which are referred to as system chaincodes. The application can further utilize smart contracts that are trusted distributed applications which leverage tamper-proof properties of the blockchain database and an underlying agreement between nodes, which is referred to as an endorsement or endorsement policy. Blockchain transactions associated with this application can be "endorsed" before being committed to the blockchain while transactions, which are not endorsed, are disregarded. An endorsement policy allows chaincodes to specify endorsers for a transaction in the form of a set of peer nodes that are necessary for endorsement. When a client sends the transaction to the peers specified in the endorsement policy, the transaction is executed to validate the transaction. After a validation, the transactions enter an ordering phase in which a consensus protocol is used to produce an ordered sequence of endorsed transactions grouped into blocks.

In the example depicted in FIG. 4, a host platform 420 (such as the CS node 102) builds and deploys a machine learning model for predictive monitoring of assets 430. Here, the host platform 420 may be a cloud platform, an industrial server, a web server, a personal computer, a user device, and the like. Assets 430 can represent diagnosis parameters. The blockchain 110 can be used to significantly improve both a training process 402 of the machine learning model and the diagnosis parameters' predictive process 405 based on a trained machine learning model. For example, in 402, rather than requiring a data scientist/engineer or other user to collect the data, historical data (heuristics—i.e., patients'-related data) may be stored by the assets 430 themselves (or through an intermediary, not shown) on the blockchain 110.

This can significantly reduce the collection time needed by the host platform 420 when performing predictive model training. For example, using smart contracts, data can be directly and reliably transferred straight from its place of origin (e.g., from the CS node 102 or from patient databases 103 and 106 depicted in FIGS. 1A-1B) to the blockchain 110. By using the blockchain 110 to ensure the security and ownership of the collected data, smart contracts may directly send the data from the assets to the entities that use the data for building a machine learning model. This allows for sharing of data among the assets 430. The collected data may be stored in the blockchain 110 based on a consensus mechanism. The consensus mechanism pulls in (permissioned nodes) to ensure that the data being recorded is verified and accurate. The data recorded is time-stamped, cryptographically signed, and immutable. It is therefore auditable, transparent, and secure.

Furthermore, training of the machine learning model on the collected data may take rounds of refinement and testing by the host platform 420. Each round may be based on additional data or data that was not previously considered to help expand the knowledge of the machine learning model. In 402, the different training and testing steps (and the data associated therewith) may be stored on the blockchain 110 by the host platform 420. Each refinement of the machine learning model (e.g., changes in variables, weights, etc.) may be stored on the blockchain 110. This provides verifiable proof of how the model was trained and what data was used to train the model. Furthermore, when the host platform 420 has achieved a finally trained model, the resulting model itself may be stored on the blockchain 110.

After the model has been trained, it may be deployed to a live environment where it can make recommendation-related predictions/decisions based on the execution of the final trained machine learning model using the prediction parameters. In this example, data fed back from the asset 430 may be input into the machine learning model and may be used to make event predictions such as most optimal treatment and treatment scheduling parameters for setting the patient interactions for the given interview data. Determinations made by the execution of the machine learning model (e.g., classification and treatment recommendations, risk assessment data, etc.) at the host platform 420 may be stored on the blockchain 110 to provide auditable/verifiable proof. As one non-limiting example, the machine learning model may predict a future change of a part of the asset 430 (the treatment recommendation parameters—i.e., assessment of risk of unsuccessful medical treatment). The data behind this decision may be stored by the host platform 420 on the blockchain 110.

As discussed above, in one embodiment, the features and/or the actions described and/or depicted herein can occur on or with respect to the blockchain 110. The above embodiments of the present disclosure may be implemented in hardware, in computer-readable instructions executed by a processor, in firmware, or in a combination of the above. The computer computer-readable instructions may be embodied on a computer-readable medium, such as a storage medium. For example, the computer computer-readable instructions may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative embodiment, the processor and the storage medium may reside as discrete components. For example, FIG. 5 illustrates an example computing device (e.g., a server node) 500, which may represent or be integrated in any of the above-described components, etc.

Figure 5:
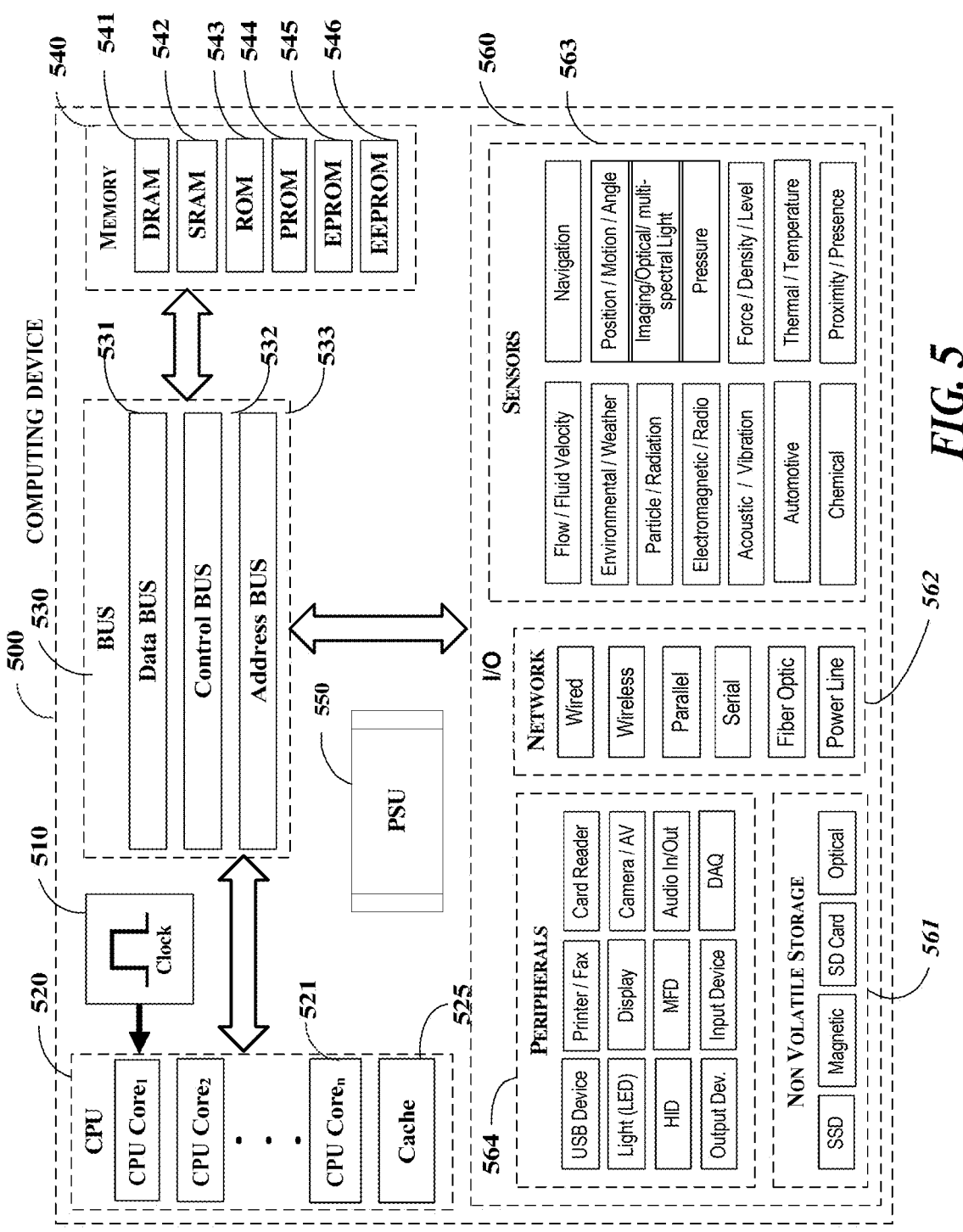
FIG. 5 illustrates a block diagram of a system including a computing device for performing the method of FIGS. 3A and 3B.

FIG. 5 illustrates a block diagram of a system including computing device 500. The computing device 500 may comprise, but not be limited to the following:

Mobile computing device, such as, but is not limited to, a laptop, a tablet, a smartphone, a drone, a wearable, an embedded device, a handheld device, an Arduino, an industrial device, or a remotely operable recording device;

A supercomputer, an exa-scale supercomputer, a mainframe, or a quantum computer;

A minicomputer, wherein the minicomputer computing device comprises, but is not limited to, an IBM AS500/iSeries/System I, A DEC VAX/PDP, a HP3000, a Honeywell-Bull DPS, a Texas Instruments TI-990, or a Wang Laboratories VS Series; or A microcomputer, wherein the microcomputer computing device comprises, but is not limited to, a server, wherein a server may be rack mounted, a workstation, an industrial device, a raspberry pi, a desktop, or an embedded device.

The CS node 102 (see FIG. 2) may be hosted on a centralized server or on a cloud computing service. Although method 300 has been described to be performed by the RS node 102 implemented on a computing device 500, it should be understood that, in some embodiments, different operations may be performed by a plurality of the computing devices 500 in operative communication at least one network.

Embodiments of the present disclosure may comprise a computing device having a central processing unit (CPU) 520, a bus 530, a memory unit 550, a power supply unit (PSU) 550, and one or more Input/Output (I/O) units. The CPU 520 coupled to the memory unit 550 and the plurality of I/O units 560 via the bus 530, all of which are powered by the PSU 550. It should be understood that, in some embodiments, each disclosed unit may actually be a plurality of such units for the purposes of redundancy, high availability, and/or performance. The combination of the presently disclosed units is configured to perform the stages of any method disclosed herein.

Consistent with an embodiment of the disclosure, the aforementioned CPU 520, the bus 530, the memory unit 550, a PSU 550, and the plurality of I/O units 560 may be implemented in a computing device, such as computing device 500. Any suitable combination of hardware, software, or firmware may be used to implement the aforementioned units. For example, the CPU 520, the bus 530, and the memory unit 550 may be implemented with computing device 500 or any of other computing devices 500, in combination with computing device 500. The aforementioned system, device, and components are examples and other systems, devices, and components may comprise the aforementioned CPU 520, the bus 530, the memory unit 550, consistent with embodiments of the disclosure.

At least one computing device 500 may be embodied as any of the computing elements illustrated in all of the attached figures, including the CS node 102 (FIG. 2). A computing device 500 does not need to be electronic, nor even have a CPU 520, nor bus 530, nor memory unit 550. The definition of the computing device 500 to a person having ordinary skill in the art is "A device that computes, especially a programmable [usually] electronic machine that performs high-speed mathematical or logical operations or that assembles, stores, correlates, or otherwise processes information." Any device which processes information qualifies as a computing device 500, especially if the processing is purposeful.

With reference to FIG. 5, a system consistent with an embodiment of the disclosure may include a computing device, such as computing device 500. In a basic configuration, computing device 500 may include at least one clock module 510, at least one CPU 520, at least one bus 530, and at least one memory unit 550, at least one PSU 550, and at least one I/O 560 module, wherein I/O module may be comprised of, but not limited to a non-volatile storage sub-module 561, a communication sub-module 562, a sensors sub-module 563, and a peripherals sub-module 565.

A system consistent with an embodiment of the disclosure the computing device 500 may include the clock module 510 may be known to a person having ordinary skill in the art as a clock generator, which produces clock signals. Clock signal is a particular type of signal that oscillates between a high and a low state and is used like a metronome to coordinate actions of digital circuits. Most integrated circuits (ICs) of sufficient complexity use a clock signal in order to synchronize different parts of the circuit, cycling at a rate slower than the worst-case internal propagation delays. The preeminent example of the aforementioned integrated circuit is the CPU 520, the central component of modern computers, which relies on a clock. The only exceptions are asynchronous circuits such as asynchronous CPUs. The clock 510 can comprise a plurality of embodiments, such as, but not limited to, single-phase clock which transmits all clock signals on effectively 1 wire, two-phase clock which distributes clock signals on two wires, each with non-overlapping pulses, and four-phase clock which distributes clock signals on 5 wires.

Many computing devices 500 use a "clock multiplier" which multiplies a lower frequency external clock to the appropriate clock rate of the CPU 520. This allows the CPU 520 to operate at a much higher frequency than the rest of the computer, which affords performance gains in situations where the CPU 520 does not need to wait on an external factor (like memory 550 or input/output 560). Some embodiments of the clock 510 may include dynamic frequency change, where the time between clock edges can vary widely from one edge to the next and back again.

A system consistent with an embodiment of the disclosure the computing device 500 may include the CPU unit 520 comprising at least one CPU Core 521. A plurality of CPU cores 521 may comprise identical CPU cores 521, such as, but not limited to, homogeneous multi-core systems. It is also possible for the plurality of CPU cores 521 to comprise different CPU cores 521, such as, but not limited to, heterogeneous multi-core systems, big.LITTLE systems and some AMD accelerated processing units (APU). The CPU unit 520 reads and executes program instructions which may be used across many application domains, for example, but not limited to, general purpose computing, embedded computing, network computing, digital signal processing (DSP), and graphics processing (GPU). The CPU unit 520 may run multiple instructions on separate CPU cores 521 at the same time. The CPU unit 520 may be integrated into at least one of a single integrated circuit die and multiple dies in a single chip package. The single integrated circuit die and multiple dies in a single chip package may contain a plurality of other aspects of the computing device 500, for example, but not limited to, the clock 510, the CPU 520, the bus 530, the memory 550, and I/O 560.

The CPU unit 520 may contain cache 522 such as, but not limited to, a level 1 cache, level 2 cache, level 3 cache or combination thereof. The aforementioned cache 522 may or may not be shared amongst a plurality of CPU cores 521. The cache 522 sharing comprises at least one of message passing and inter-core communication methods may be used for the at least one CPU Core 521 to communicate with the cache 522. The inter-core communication methods may comprise, but not limited to, bus, ring, two-dimensional mesh, and crossbar. The aforementioned CPU unit 520 may employ symmetric multiprocessing (SMP) design.

The plurality of the aforementioned CPU cores 521 may comprise soft microprocessor cores on a single field programmable gate array (FPGA), such as semiconductor intellectual property cores (IP Core). The plurality of CPU cores 521 architecture may be based on at least one of, but not limited to, Complex instruction set computing (CISC), Zero instruction set computing (ZISC), and Reduced instruction set computing (RISC). At least one of the performance-enhancing methods may be employed by the plurality of the CPU cores 521, for example, but not limited to Instruction-level parallelism (ILP) such as, but not limited to, super-scalar pipelining, and Thread-level parallelism (TLP).

Consistent with the embodiments of the present disclosure, the aforementioned computing device 500 may employ a communication system that transfers data between components inside the aforementioned computing device 500, and/or the plurality of computing devices 500. The aforementioned communication system will be known to a person having ordinary skill in the art as a bus 530. The bus 530 may embody internal and/or external plurality of hardware and software components, for example, but not limited to a wire, optical fiber, communication protocols, and any physical arrangement that provides the same logical function as a parallel electrical bus. The bus 530 may comprise at least one of, but not limited to a parallel bus, wherein the parallel bus carry data words in parallel on multiple wires, and a serial bus, wherein the serial bus carry data in bit-serial form. The bus 530 may embody a plurality of topologies, for example, but not limited to, a multidrop/electrical parallel topology, a daisy chain topology, and a connected by switched hubs, such as USB bus. The bus 530 may comprise a plurality of embodiments, for example, but not limited to:

Internal data bus (data bus) 531/Memory bus
    Control bus 532
    Address bus 533
    System Management Bus (SM Bus)
    Front-Side-Bus (FSB)
    External Bus Interface (EBI)
    Local bus
    Expansion bus
    Lightning bus
    Controller Area Network (CAN bus)

Camera Link

ExpressCard

Advanced Technology management Attachment (ATA), including embodiments and derivatives such as, but not limited to, Integrated Drive Electronics (IDE)/Enhanced IDE (EIDE), ATA Packet Interface (ATAPI), Ultra-Direct Memory Access (UDMA), Ultra ATA (UATA)/Parallel ATA (PATA)/Serial ATA (SATA), CompactFlash (CF) interface, Consumer Electronics ATA (CE-ATA)/Fiber Attached Technology Adapted (FATA), Advanced Host Controller Interface (AHCI), SATA Express (SATAe)/External SATA (eSATA), including the powered embodiment eSATAp/Mini-SATA (mSATA), and Next Generation Form Factor (NGFF)/M.2.

Small Computer System Interface (SCSI)/Serial Attached SCSI (SAS)

HyperTransport

InfiniBand

RapidIO

Mobile Industry Processor Interface (MIPI)

Coherent Processor Interface (CAPI)

Plug-n-play

1-Wire

Peripheral Component Interconnect (PCI), including embodiments such as, but not limited to, Accelerated Graphics Port (AGP), Peripheral Component Interconnect eX tended (PCI-X), Peripheral Component Interconnect Express (PCI-e) (e.g., PCI Express Mini Card, PCI Express M.2 [Mini PCIe v2], PCI Express External Cabling [ePCIe], and PCI Express OCuLink [Optical Copper {Cu} Link]), Express Card, AdvancedTCA, AMC, Universal IO, Thunderbolt/Mini DisplayPort, Mobile PCIe (M-PCIe), U.2, and Non-Volatile Memory Express (NVMe)/Non-Volatile Memory Host Controller Interface Specification (NVMHCIS).

Industry Standard Architecture (ISA), including embodiments such as, but not limited to Extended ISA (EISA), PC/XT-bus/PC/AT-bus/PC/105 bus (e.g., PC/105-Plus, PCI/105-Express, PCI/105, and PCI-105), and Low Pin Count (LPC).

Music Instrument Digital Interface (MIDI)

Universal Serial Bus (USB), including embodiments such as, but not limited to, Media Transfer Protocol (MTP)/Mobile High-Definition Link (MHL), Device Firmware Upgrade (DFU), wireless USB, InterChip USB, IEEE 1395 Interface/Firewire, Thunderbolt, and eX tensible Host Controller Interface (xHCI).

Consistent with the embodiments of the present disclosure, the aforementioned computing device 500 may employ hardware integrated circuits that store information for immediate use in the computing device 500, known to the person having ordinary skill in the art as primary storage or memory 550. The memory 550 operates at high speed, distinguishing it from the non-volatile storage sub-module 561, which may be referred to as secondary or tertiary storage, which provides slow-to-access information but offers higher capacities at lower cost. The contents contained in memory 550, may be transferred to secondary storage via techniques such as, but not limited to, virtual memory and swap. The memory 550 may be associated with addressable semiconductor memory, such as integrated circuits consisting of silicon-based transistors, used for example as primary storage but also other purposes in the computing device 500. The memory 550 may comprise a plurality of embodiments, such as, but not limited to volatile memory, non-volatile memory, and semi-volatile memory. It should be understood by a person having ordinary skill in the art that the ensuing are non-limiting examples of the aforementioned memory:

Volatile memory which requires power to maintain stored information, for example, but not limited to, Dynamic Random-Access Memory (DRAM) 551, Static Random-Access Memory (SRAM) 552, CPU Cache memory 525, Advanced Random-Access Memory (A-RAM), and other types of primary storage such as Random-Access Memory (RAM).

Non-volatile memory which can retain stored information even after power is removed, for example, but not limited to, Read-Only Memory (ROM) 553, Programmable ROM (PROM) 555, Erasable PROM (EPROM) 555, Electrically Erasable PROM (EEPROM) 556 (e.g., flash memory and Electrically Alterable PROM [EAPROM]), Mask ROM (MROM), One Time Programmable (OTP) ROM/Write Once Read Many (WORM), Ferroelectric RAM (FeRAM), Parallel Random-Access Machine (PRAM), Split-Transfer Torque RAM (STT-RAM), Silicon Oxime Nitride Oxide Silicon (SONOS), Resistive RAM (RRAM), Nano RAM (NRAM), 3D X Point, Domain-Wall Memory (DWM), and millipede memory.

Semi-volatile memory which may have some limited non-volatile duration after power is removed but loses data after said duration has passed. Semi-volatile memory provides high performance, durability, and other valuable characteristics typically associated with volatile memory, while providing some benefits of true non-volatile memory. The semi-volatile memory may comprise volatile and non-volatile memory and/or volatile memory with battery to provide power after power is removed. The semi-volatile memory may comprise, but not limited to spin-transfer torque RAM (STT-RAM).

Consistent with the embodiments of the present disclosure, the aforementioned computing device 500 may employ the communication system between an information processing system, such as the computing device 500, and the outside world, for example, but not limited to, human, environment, and another computing device 500. The aforementioned communication system will be known to a person having ordinary skill in the art as I/O 560. The I/O module 560 regulates a plurality of inputs and outputs with regard to the computing device 500, wherein the inputs are a plurality of signals and data received by the computing device 500, and the outputs are the plurality of signals and data sent from the computing device 500. The I/O module 560 interfaces a plurality of hardware, such as, but not limited to, non-volatile storage 561, communication devices 562, sensors 563, and peripherals 565. The plurality of hardware is used by at least one of, but not limited to, human, environment, and another computing device 500 to communicate with the present computing device 500. The I/O module 560 may comprise a plurality of forms, for example, but not limited to channel I/O, port mapped I/O, asynchronous I/O, and Direct Memory Access (DMA).

Consistent with the embodiments of the present disclosure, the aforementioned computing device 500 may employ the non-volatile storage sub-module 561, which may be referred to by a person having ordinary skill in the art as one of secondary storage, external memory, tertiary storage, off-line storage, and auxiliary storage. The non-volatile storage sub-module 561 may not be accessed directly by the CPU 520 without using an intermediate area in the memory 550. The non-volatile storage sub-module 561 does not lose data when power is removed and may be two orders of magnitude less costly than storage used in memory modules, at the expense of speed and latency. The non-volatile storage sub-module 561 may comprise a plurality of forms, such as, but not limited to, Direct Attached Storage (DAS), Network Attached Storage (NAS), Storage Area Network (SAN), nearline storage, Massive Array of Idle Disks (MAID), Redundant Array of Independent Disks (RAID), device mirroring, off-line storage, and robotic storage. The non-volatile storage sub-module (561) may comprise a plurality of embodiments, such as, but not limited to:

Optical storage, for example, but not limited to, Compact Disk (CD) (CD-ROM/CD-R/CD-RW), Digital Versatile Disk (DVD) (DVD-ROM/DVD-R/DVD+R/DVD-RW/DVD+RW/DVD+RW/DVD+R DL/DVD-RAM/HD-DVD), Blu-ray Disk (BD) (BD-ROM/BD-R/BD-RE/BD-R DL/BD-RE DL), and Ultra-Density Optical (UDO).

Semiconductor storage, for example, but not limited to, flash memory, such as, but not limited to, USB flash drive, Memory card, Subscriber Identity Module (SIM) card, Secure Digital (SD) card, Smart Card, Compact-Flash (CF) card, Solid-State Drive (SSD) and memristor.

Magnetic storage such as, but not limited to, Hard Disk Drive (HDD), tape drive, carousel memory, and Card Random-Access Memory (CRA M).

Phase-change memory

Holographic data storage such as Holographic Versatile Disk (HVD).

Molecular Memory

Deoxyribonucleic Acid (DNA) digital data storage

Consistent with the embodiments of the present disclosure, the aforementioned computing device 500 may employ the communication sub-module 562 as a subset of the I/O 560, which may be referred to by a person having ordinary skill in the art as at least one of, but not limited to, computer network, data network, and network. The network allows computing devices 500 to exchange data using connections, which may be known to a person having ordinary skill in the art as data links, between network nodes. The nodes comprise network computer devices 500 that originate, route, and terminate data. The nodes are identified by network addresses and can include a plurality of hosts consistent with the embodiments of a computing device 500. The aforementioned embodiments include, but not limited to personal computers, phones, servers, drones, and networking devices such as, but not limited to, hubs, switches, routers, modems, and firewalls.

Two nodes can be networked together, when one computing device 500 is able to exchange information with the other computing device 500, whether or not they have a direct connection with each other. The communication sub-module 562 supports a plurality of applications and services, such as, but not limited to World Wide Web (WWW), digital video and audio, shared use of application and storage computing devices 500, printers/scanners/fax machines, email/online chat/instant messaging, remote control, distributed computing, etc. The network may comprise a plurality of transmission mediums, such as, but not limited to conductive wire, fiber optics, and wireless. The network may comprise a plurality of communications protocols to organize network traffic, wherein application-specific communications protocols are layered, may be known to a person having ordinary skill in the art as carried as payload, over other more general communications protocols. The plurality of communications protocols may comprise, but not limited to, IEEE 802, ethernet, Wireless LAN (WLAN/Wi-Fi), Internet Protocol (IP) suite (e.g., TCP/IP, UDP, Internet Protocol version 5 [IPv5], and Internet Protocol version 6 [IPv6]), Synchronous Optical Networking (SONET)/Synchronous Digital Hierarchy (SDH), Asynchronous Transfer Mode (ATM), and cellular standards (e.g., Global System for Mobile Communications [GSM], General Packet Radio Service [GPRS], Code-Division Multiple Access [CDMA], and Integrated Digital Enhanced Network [IDEN]).

The communication sub-module 562 may comprise a plurality of size, topology, traffic control mechanism and organizational intent. The communication sub-module 562 may comprise a plurality of embodiments, such as, but not limited to:

Wired communications, such as, but not limited to, coaxial cable, phone lines, twisted pair cables (ethernet), and InfiniBand.

Wireless communications, such as, but not limited to, communications satellites, cellular systems, radio frequency/spread spectrum technologies, IEEE 802.11 Wi-Fi, Bluetooth, NFC, free-space optical communications, terrestrial microwave, and Infrared (IR) communications. Cellular systems embody technologies such as, but not limited to, 3G, 5G (such as WiMax and LTE), and 5G (short and long wavelength).

Parallel communications, such as, but not limited to, LPT ports.

Serial communications, such as, but not limited to, RS-232 and USB.

Fiber Optic communications, such as, but not limited to, Single-mode optical fiber (SMF) and Multi-mode optical fiber (MMF).

Power Line and wireless communications

The aforementioned network may comprise a plurality of layouts, such as, but not limited to, bus network such as ethernet, star network such as Wi-Fi, ring network, mesh network, fully connected network, and tree network. The network can be characterized by its physical capacity or its organizational purpose. Use of the network, including user authorization and access rights, differ accordingly. The characterization may include, but not limited to nanoscale network, Personal Area Network (PAN), Local Area Network (LAN), Home Area Network (HAN), Storage Area Network (SAN), Campus Area Network (CAN), backbone network, Metropolitan Area Network (MAN), Wide Area Network (WAN), enterprise private network, Virtual Private Network (VPN), and Global Area Network (GAN).

Consistent with the embodiments of the present disclosure, the aforementioned computing device 500 may employ the sensors sub-module 563 as a subset of the I/O 560. The sensors sub-module 563 comprises at least one of the devices, modules, and subsystems whose purpose is to detect events or changes in its environment and send the information to the computing device 500. Sensors are sensitive to the measured property, are not sensitive to any property not measured, but may be encountered in its application, and do not significantly influence the measured property. The sensors sub-module 563 may comprise a plurality of digital devices and analog devices, wherein if an analog device is used, an Analog to Digital (A-to-D) converter must be employed to interface the said device with the computing device 500. The sensors may be subject to a plurality of deviations that limit sensor accuracy. The sensors sub-module 563 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors. It should be understood by a person having ordinary skill in the art that the ensuing are non-limiting examples of the aforementioned sensors:

Chemical sensors, such as, but not limited to, breathalyzer, carbon dioxide sensor, carbon monoxide/smoke detector, catalytic bead sensor, chemical field-effect transistor, chemiresistor, electrochemical gas sensor, electronic nose, electrolyte-insulator-semiconductor sensor, energy-dispersive X-ray spectroscopy, fluorescent chloride sensors, holographic sensor, hydrocarbon dew point analyzer, hydrogen sensor, hydrogen sulfide sensor, infrared point sensor, ion-selective electrode, nondispersive infrared sensor, microwave chemistry sensor, nitrogen oxide sensor, olfactometer, optode, oxygen sensor, ozone monitor, pellistor, pH glass electrode, potentiometric sensor, redox electrode, zinc oxide nanorod sensor, and biosensors (such as nanosensors).

Automotive sensors, such as, but not limited to, air flow meter/mass airflow sensor, air-fuel ratio meter, AFR sensor, blind spot monitor, engine coolant/exhaust gas/cylinder head/transmission fluid temperature sensor, hall effect sensor, wheel/automatic speed sensor, airbag sensors, brake fluid/engine transmission/turbine/vehicle crankcase/fuel/oil/tire pressure sensor, camshaft/crankshaft/throttle position sensor, fuel/oil level sensor, knock sensor, light sensor, MA P sensor, oxygen sensor (o2), parking sensor, radar sensor, torque sensor, variable reluctance sensor, and water-in-fuel sensor.

Acoustic, sound and vibration sensors, such as, but not limited to, microphone, lace sensor (guitar pickup), seismometer, sound locator, geophone, and hydrophone.

Electric current, electric potential, magnetic, and radio sensors, such as, but not limited to, current sensor, Daly detector, electroscope, electron multiplier, faraday cup, galvanometer, hall effect sensor, hall probe, magnetic anomaly detector, magnetometer, magnetoresistance, MEMS magnetic field sensor, metal detector, planar hall sensor, radio direction finder, and voltage detector.

Environmental, weather, moisture, and humidity sensors, such as, but not limited to, actinometer, air pollution sensor, bedwetting alarm, ceilometer, dew warning, electrochemical gas sensor, fish counter, frequency domain sensor, gas detector, hook gauge evaporimeter, humistor, hygrometer, leaf sensor, lysimeter, pyranometer, pyrgeometer, psychrometer, rain gauge, rain sensor, seismometers, SNOTEL, snow gauge, soil moisture sensor, stream gauge, and tide gauge.

Flow and fluid velocity sensors, such as, but not limited to, air flow meter, anemometer, flow sensor, gas meter, mass flow sensor, and water meter.

Ionizing radiation and particle sensors, such as, but not limited to, cloud chamber, Geiger counter, Geiger-Muller tube, ionization chamber, neutron detection, proportional counter, scintillation counter, semiconductor detector, and thermoluminescent dosimeter.

Navigation sensors, such as, but not limited to, air speed indicator, altimeter, attitude indicator, depth gauge, fluxgate compass, gyroscope, inertial navigation system, inertial reference unit, magnetic compass, MHD sensor, ring laser gyroscope, turn coordinator, variometer, vibrating structure gyroscope, and yaw rate sensor.

Position, angle, displacement, distance, speed, and acceleration sensors, such as, but not limited to, accelerometer, displacement sensor, flex sensor, free fall sensor, gravimeter, impact sensor, laser rangefinder, LIDAR, odometer, photoelectric sensor, position sensor such as, but not limited to, GPS or Glonass, angular rate sensor, shock detector, ultrasonic sensor, tilt sensor, tachometer, ultra-wideband radar, variable reluctance sensor, and velocity receiver.

Imaging, optical and light sensors, such as, but not limited to, CMOS sensor, LiDAR, multi-spectral light sensor, colorimeter, contact image sensor, electro-optical sensor, infra-red sensor, kinetic inductance detector, LED as light sensor, light-addressable potentiometric sensor, Nichols radiometer, fiber-optic sensors, optical position sensor, thermopile laser sensor, photodetector, photodiode, photomultiplier tubes, phototransistor, photoelectric sensor, photoionization detector, photomultiplier, photoresistor, photoswitch, phototube, scintillometer, Shack-Hartmann, single-photon avalanche diode, superconducting nanowire single-photon detector, transition edge sensor, visible light photon counter, and wavefront sensor.

Pressure sensors, such as, but not limited to, barograph, barometer, boost gauge, bourdon gauge, hot filament ionization gauge, ionization gauge, McLeod gauge, Oscillating U-tube, permanent downhole gauge, piezometer, Pirani gauge, pressure sensor, pressure gauge, tactile sensor, and time pressure gauge.

Force, Density, and Level sensors, such as, but not limited to, bhangmeter, hydrometer, force gauge or force sensor, level sensor, load cell, magnetic level or nuclear density sensor or strain gauge, piezo capacitive pressure sensor, piezoelectric sensor, torque sensor, and viscometer.

Thermal and temperature sensors, such as, but not limited to, bolometer, bimetallic strip, calorimeter, exhaust gas temperature gauge, flame detection/pyrometer, Gardon gauge, Golay cell, heat flux sensor, microbolometer, microwave radiometer, net radiometer, infrared/quartz/resistance thermometer, silicon bandgap temperature sensor, thermistor, and thermocouple.

Proximity and presence sensors, such as, but not limited to, alarm sensor, doppler radar, motion detector, occupancy sensor, proximity sensor, passive infrared sensor, reed switch, stud finder, triangulation sensor, touch switch, and wired glove.

Consistent with the embodiments of the present disclosure, the aforementioned computing device 500 may employ the peripherals sub-module 562 as a subset of the I/O 560. The peripheral sub-module 565 comprises ancillary devices used to put information into and get information out of the computing device 500. There are 3 categories of devices comprising the peripheral sub-module 565, which exist based on their relationship with the computing device 500, input devices, output devices, and input/output devices. Input devices send at least one of data and instructions to the computing device 500. Input devices can be categorized based on, but not limited to:

Modality of input, such as, but not limited to, mechanical motion, audio, visual, and tactile.

Whether the input is discrete, such as but not limited to, pressing a key, or continuous such as, but not limited to position of a mouse.

The number of degrees of freedom involved, such as, but not limited to, two-dimensional mice vs three-dimensional mice used for Computer-Aided Design (CAD) applications.

Output devices provide output from the computing device 500. Output devices convert electronically generated information into a form that can be presented to humans. Input/output devices that perform both input and output functions. It should be understood by a person having ordinary skill in the art that the ensuing are non-limiting embodiments of the aforementioned peripheral sub-module 565:

Input Devices:

Human Interface Devices (HID), such as, but not limited to, pointing device (e.g., mouse, touchpad, joystick, touchscreen, game controller/gamepad, remote, light pen, light gun, Wii remote, jog dial, shuttle, and knob), keyboard, graphics tablet, digital pen, gesture recognition devices, magnetic ink character recognition, Sip-and-Puff (SNP) device, and Language Acquisition Device (LAD).

High degree of freedom devices, that require up to six degrees of freedom such as, but not limited to, camera gimbals, Cave Automatic Virtual Environment (CAVE), and virtual reality systems.

Video Input devices are used to digitize images or video from the outside world into the computing device 500. The information can be stored in a multitude of formats depending on the user's requirement. Examples of types of video input devices include, but not limited to, digital camera, digital camcorder, portable media player, webcam, Microsoft Kinect, image scanner, fingerprint scanner, barcode reader, 3D scanner, laser rangefinder, eye gaze tracker, computed tomography, magnetic resonance imaging, positron emission tomography, medical ultrasonography, TV tuner, and iris scanner.

Audio input devices are used to capture sound. In some cases, an audio output device can be used as an input device, in order to capture produced sound. Audio input devices allow a user to send audio signals to the computing device 500 for at least one of processing, recording, and carrying out commands. Devices such as microphones allow users to speak to the computer in order to record a voice message or navigate software. Aside from recording, audio input devices are also used with speech recognition software. Examples of types of audio input devices include, but not limited to microphone, Musical Instrument Digital Interface (MIDI) devices such as, but not limited to a keyboard, and headset.

Data Acquisition (DAQ) devices convert at least one of analog signals and physical parameters to digital values for processing by the computing device 500. Examples of DAQ devices may include, but not limited to, Analog to Digital Converter (ADC), data logger, signal conditioning circuitry, multiplexer, and Time to Digital Converter (TDC).

Output Devices may further comprise, but not be limited to:

Display devices, which convert electrical information into visual form, such as, but not limited to, monitor, TV, projector, and Computer Output Microfilm (COM). Display devices can use a plurality of underlying technologies, such as, but not limited to, Cathode-Ray Tube (CRT), Thin-Film Transistor (TFT), Liquid Crystal Display (LCD), Organic Light-Emitting Diode (OLED), MicroLED, E Ink Display (ePaper) and Refreshable Braille Display (Braille Terminal).

Printers, such as, but not limited to, inkjet printers, laser printers, 3D printers, solid ink printers and plotters.

Audio and Video (AV) devices, such as, but not limited to, speakers, headphones, amplifiers and lights, which include lamps, strobes, DJ lighting, stage lighting, architectural lighting, special effect lighting, and lasers.

Other devices such as Digital to Analog Converter (DAC)

Input/Output Devices may further comprise, but not be limited to, touchscreens, networking device (e.g., devices disclosed in network 562 sub-module), data storage device (non-volatile storage 561), facsimile (FAX), and graphics/sound cards.

All rights including copyrights in the code included herein are vested in and the property of the Applicant. The Applicant retains and reserves all rights in the code included herein, and grants permission to reproduce the material only in connection with reproduction of the granted patent and for no other purpose.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

What is claimed is:

1. A system comprising:

at least one biosensor;

a microphone;

at least one processor; and a memory communicatively coupled to the at least one processor, the memory storing non-transitory machine-readable instructions that, when executed by the processor, cause the processor to perform operations comprising:

receiving, from the at least one biosensor, sensory data, the sensory data comprising at least one of heart rate, blood oxygen saturation, or body temperature of a user wearing a wearable device comprising the at least one biosensor;

receiving, from the microphone, audio data based on speech of the user;

transcribing the audio data, resulting in transcribed audio;

retrieving, from at least one database, demographic information of previous patients associated with the user;

generating a first feature vector based on the sensory data, the transcribed audio, and the demographic information;

executing an artificial intelligence (AI) algorithm, wherein:

inputs to the AI algorithm comprise the first feature vector; and output of the AI algorithm comprises a predictive model;

generating an updated feature vector based on additional sensor data acquired after receiving the sensory data and additional transcribed audio data acquired after receiving the audio data; and providing the updated feature vector to the AI algorithm, wherein the AI algorithm executes the predictive model to produce a predicted illness and a treatment recommendation for the predicted illness.

2. The system of claim 1, wherein the at least one processor is configured to determine whether the sensory data deviates from a prior recorded value by more than a predefined threshold.

3. The system of claim 2, wherein the processor is configured to, responsive to detecting a deviation from the predefined threshold, re-execute the AI algorithm using predictive model and updated sensory data.

4. The system of claim 1, wherein the predicted illness is stored on a blockchain ledger in association with selected features derived from the transcribed audio.

5. The system of claim 4, wherein the at least one a memory has stored additional non-transitory machine-readable instructions that, when executed by the processor, cause the processor to perform operations comprising:

generating the selected features based at least in part on the audio data, wherein the audio data is collected during an interaction between the user and a chat bot; and deriving a plurality of key features from the transcribed audio prior to the generating of the first feature vector, wherein the first feature vector is further based on the plurality of key features.

6. A method comprising:

receiving, at a computer system from a plurality of biosensors of a wearable device, sensory data, the sensory data comprising at least one of heart rate, blood oxygen saturation, or body temperature of a user wearing the wearable device;

receiving, at the computer system, audio data generated based on speech of the user;

transcribing, via at least one processor of the computer system, the audio data, resulting in transcribed audio;

retrieving, via the at least one processor from at least one database, demographic information of previous patients associated with the user;

generating a first feature vector based on the sensory data, the transcribed audio, and the demographic information;

executing, via the at least one processor, an artificial intelligence (AI) algorithm, wherein:

inputs to the AI algorithm comprise the first feature vector; and output of the AI algorithm comprises a predictive model;

generating an updated feature vector based on additional sensor data acquired after receiving the sensory data and additional transcribed audio data acquired after receiving the audio data; and providing the updated feature vector to the AI algorithm, wherein the AI algorithm executes the predictive model to produce a predicted illness and a treatment recommendation for the predicted illness.

7. The method of claim 6, further comprising: monitoring the sensory data of the user to determine whether the sensory data deviates from a prior recorded value by more than a predefined threshold.

8. The method of claim 7, further comprising responsive to detecting a deviation from the predefined threshold, re-executing the AI algorithm using the predictive model and updated sensory data.

9. The method of claim 6, further comprising storing the predicted illness on a blockchain ledger in association with selected features derived from the transcribed audio.

10. The method of claim 9, wherein generating of the selected features comprises processing the audio data, wherein the audio data is collected during an interaction between the user and a chat bot.

11. A non-transitory computer-readable medium having instructions stored which, when executed by at least one processor, cause the at least one processor to perform operations comprising:

receiving, from at least one biosensor, sensory data, the sensory data comprising at least one of heart rate, blood oxygen saturation, or body temperature of a user wearing a wearable device comprising the at least one biosensor;

receiving, from a microphone, audio data based on speech of the user;

transcribing the audio data, resulting in transcribed audio;

retrieving, from at least one database, demographic information of previous patients associated with the user;

generating a first feature vector based on the sensory data, the transcribed audio, and the demographic information;

executing an artificial intelligence (AI) algorithm, wherein:

inputs to the AI algorithm comprise the first feature vector; and output of the AI algorithm comprises a predictive model;

generating an updated feature vector based on additional sensor data acquired after receiving the sensory data and additional transcribed audio data acquired after receiving the audio data; and providing the updated feature vector to the AI algorithm, wherein the AI algorithm executes the predictive model to produce a predicted illness and a treatment recommendation for the predicted illness.

12. The non-transitory computer-readable medium of claim 11, having additional instructions stored which, when executed by the at least one processor, cause the at least one processor to perform operations comprising:

monitoring the sensory data to determine whether the sensory data deviates from a prior recorded value by more than a predefined threshold.

13. The non-transitory computer-readable medium of claim 12, having additional instructions stored which, when executed by the at least one processor, cause the at least one processor to perform operations comprising: upon detecting a deviation from the predefined threshold, re-executing the AI algorithm using the predictive model and updated sensory data.

14. The non-transitory computer-readable medium of claim 11, having additional instructions stored which, when executed by the at least one processor, cause the at least one processor to perform operations comprising:

storing the predicted illness on a blockchain ledger in association with selected features derived from the transcribed audio.

15. The system of claim 1, wherein the AI algorithm comprises a neural network.

16. The system of claim 1, wherein the sensor data, the transcribed audio, and the demographic information comprise training data for the predictive model.

17. The method of claim 6, wherein the AI algorithm comprises a neural network.

18. The method of claim 6, wherein the sensor data, the transcribed audio, and the demographic information comprise training data for the predictive model.

19. The system of claim 5, wherein the key features are derived, at least in part, based on a language of the speech of the user; and wherein the key features are extracted from the transcribed audio based on keyword matching from notes associated with the user.

20. The system of claim 19, wherein the predicted illness is sepsis, and wherein the predictive model is configured to perform sepsis risk assessment modeling based at least in part on the key features and the sensory data.

* * * * *